United States Patent [19]

Caporiccio et al.

[11] Patent Number: 4,808,472
[45] Date of Patent: Feb. 28, 1989

[54] FLUOROPOLYETHERS CONTAINING END GROUPS ENDOWED WITH ANCHORING CAPACITY

[75] Inventors: Gerardo Caporiccio, Milan; Ezio Strepparola, Treviglio; Mario A. Scarati, Milan, all of Italy

[73] Assignee: Montedison S.p.A., Milan, Italy

[21] Appl. No.: 111,607

[22] Filed: Oct. 23, 1987

Related U.S. Application Data

[62] Division of Ser. No. 687,844, Dec. 31, 1984, Pat. No. 4,721,795.

[30] Foreign Application Priority Data

Jun. 19, 1984 [IT] Italy .................... 21481 A/84

[51] Int. Cl.$^4$ .................................. G11B 5/71
[52] U.S. Cl. ............................ 428/336; 427/128; 427/131; 427/132; 428/421; 428/422; 428/694; 428/695; 428/900
[58] Field of Search .......... 428/694, 695, 900, 421, 428/422, 64, 65, 336; 427/128, 132, 131; 252/67-54; 360/134-136

[56] References Cited

U.S. PATENT DOCUMENTS

| | | | |
|---|---|---|---|
| 4,267,238 | 5/1981 | Chernega | 428/480 |
| 4,268,556 | 5/1981 | Pedrotty | 428/900 |
| 4,692,378 | 8/1987 | Ishihara | 428/421 |
| 4,696,845 | 9/1987 | Yanagisawa | 428/422 |
| 4,722,859 | 2/1988 | Kudo | 428/421 |

*Primary Examiner*—Ellis P. Robinson
*Attorney, Agent, or Firm*—Stevens, Davis, Miller & Mosher

[57] ABSTRACT

Compounds suitable for being used as lubricants, having general formula:

$$RO-(C_3F_6O)_m-(CFXO)_n-CFX-L, \quad (I)$$

or $$R''CFXO-(C_3F_6O)_x(CFXO)_y-(C_2F_4O)_z-CFX-L, \quad (II)$$

where
  $R = -CF_3, -C_2F_5, -C_3F_7$
  $X = F, -CF_3$
  $R'' = F, -CF_3, -C_2F_5$
  $m =$ an integer from 3 to 100
  $n =$ a finite integer, or $=$ zero, wherefore $m+n$ ranges from 3 to 100, provided that, if n is finite, $m/n$ ranges from 5 to 20 and R is preferably $=CF_3$, if $n=$zero, R is preferably $-C_2F_5$ or $-C_3F_7$
  $x =$ a finite integer, or $=$ zero
  $y, z =$ finite integers, such that $x+y+z$ ranges from 5 to 200, while $(x+z)/y$ ranges from 5 to 0.5, provided that when $x=$zero, $z/y$ ranges from 1 to 0.05 and $y+z$ ranges from 5 to 200 n while X is preferably F, and $R''=L$
  $L =$ group A—Y, where
    $A = -CH_2O-, \quad -CH_2-O-CH_2, \quad -CF_2, -CF_2O,$
  $Y =$ an organic radical covered by one of the following formulas:

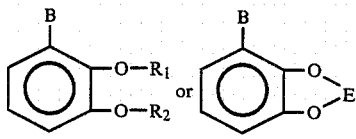

$R_1, R_2 =$ alkyls $C_1-C_3$,
  $E = CHR_3$ or $-CH_2-CHR_3$
  $B = H$ or a radical $OR_3$,
  $R_3 = H$ or an alkyl $C_1-C_3$.

2 Claims, No Drawings

FLUOROPOLYETHERS CONTAINING END GROUPS ENDOWED WITH ANCHORING CAPACITY

This is a division of application Ser. No. 687,844 filed Dec. 31, 1984, now U.S. Pat. No. 4,721,795.

THE PRIOR ART

It is known to use perfluoropolyethers as lubricants, for example in the field of the video and audio tapes, as well as in the precision mechanical instruments subjected to mechanical wear, and in the electric sector, for the protection of contacts subjected to a high number of opening-closing cycles.

Perfluoropolyethers used to such purposes are known in commerce under the trade name "Fomblin" (of Montedison) and Krytox (Du Pont), and are described for example in U.S. Pat. Nos. 3,242,218; 3,665,041 and 3,715,378.

Improvements in the lubricating properties of the perfluoropolyethers were achieved, according to what is described in U.S. Pat. Nos. 4,268,556 and 4,267,238, by introducing, into the perfluoropolyethereal chain, end groups of polar and reactive nature, of the type $-CH_2OH$, $-COOR$, $-CONH-R$, $-CO-CF_3$, which should assure a better adhesion of the perfluoropolyethereal compound to the surface to be lubricated.

However, such modification involves the drawback of a high reactivity of the intermediate groups, some of which, for example, easily hydrolyze with formation of acid groups which react with the materials, especially with the metallic ones, of the surfaces onto which they are laid, thus altering them.

THE PRESENT INVENTION

The object of the present invention is a new class of compounds having the structure of perfluoropolyethers, which exhibit better lubricating properties as well as better protective properties than the perfluoropolyethers used so far, and which at the same time are free from the drawbacks described hereinbefore. As a general structure, such compounds consist of a perfluoropolyethereal chain, characterized by the presence of proper organic end groups.

A further object of the present invention is the process for the manufacture of the above said compounds.

Such compounds can be represented by one of the following general formulas (I) and (II):

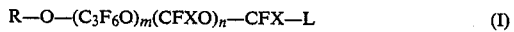

R—O—(C₃F₆O)ₘ(CFXO)ₙ—CFX—L    (I)

in which the groups ($C_3F_6O$) and (CFXO) are statistically distributed in the chain, and where:
R may be one of the groups: $-CF_3$, $-C_2F_5$, $-C_3F_7$,
X may be F or $-CF_3$
m=a finite number ranging from 3 to 100
n=a finite number or a number equal to zero, wherefore m+n ranges from 3 to 100, and preferably from 5 to 50, extremes included, provided that when n is finite, the ratio m/n ranges from 5 to 20, extremes included, and R is preferably group $-CF_3$, while when n=0, R is preferably one of the groups $-C_2F_5$ or $-C_3F_7$.

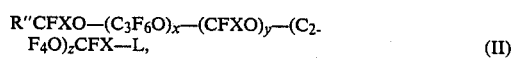

R″CFXO—(C₃F₆O)ₓ—(CFXO)ᵧ—(C₂F₄O)ᵤCFX—L,    (II)

where groups ($C_3F_6O$), (CFXO) and ($C_2F_4O$) are distributed at random in the chain, and where:
X may be F or $-CF_3$;
R″ may be F, $-CF_3$, $-C_2F_5$, provided that group R″CFX contains no more than 3 carbon atoms:
y, z=finite integers;
x=a finite integer, or it may be=0;
x+y+z varies from 5 to 200, and preferably from 5 to 100, extremes included;
the ratio (x+z)/y varies from 5 to 0.5 and preferably from 2 to 0.6, extremes included:
provided when x=0, the x/y ratio ranges from 1 to 0.5, extremes included, while the sum y+z ranges from 5 to 200, extremes included, and X is preferably F, and R″=L.

In general formulas (I) and (II), groups L are organic, non polymerisable groups, having formula:

A—Y    (III)

where:
A=$-CH_2O-$; $-CH_2-O-CH_2-$, $-CF_2-$, $-CF_2O-$,
Y=an organic non-fluorinated radical, covered by one of the following two general formulas:

(IV)

(V)

where:
R₁, R₂, like or unlike each other, are alkyl radicals containing from 1 to 3 carbon atoms;
E=group $-CHR_3-$ or $-CH_2-CHR_3-$,
R₃=H, or an alkyl radical containing from 1 to 3 carbon atoms;
B=H, or a radical O—R₃.
Preferably, radical Y exhibits the formula:

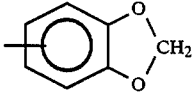

The compounds of formulas (I) and (II), thanks to group L present therein, have the property of anchoring to the surfaces of the metals or of the products indicated in groups (a), (b), (c) and (d). Such surfaces may be pure surfaces directly exposed to the contact of foreign agents and bodies, or they may be coated by thin and discrete layers of protective materials, such as resins, amorphous carbon, graphite, etc.

Particular examples of surfaces of the chemical individuals listed under (a) are the surfaces of steels, bronzes, brasses, even sintered, the surfaces of Sn—Ag, Sn—Au, Sn—Sb alloys, the surfaces of alloys such as Co—Cr, Co—Ni, Fe—Co—Ni, Co—Ni—P, deposited by sputtering or electrochemically, or, at last, the surfaces consisting of fine metal powders dispersed in a polymeric matrix.

Examples of surfaces of the chemical individuals listed under (b) are the surfaces of the materials obtained from the spreading of suspensions of pigments such as $Fe_2O_3$, $CrO_2$, $Ba(FeO_2)_2$ in polymeric matrices such as polyvinyl chloride, polyvinyl acetate, or thermosetting matrices such as polyurethane or epoxy resins, spread on carriers based on polyester, polyamide resins, or on metal carriers such as e.g. Al.

Examples of surfaces of the chemical individuals listed under (c) are the ones of ceramic materials of the type of synthetic $Al_2O_3$ (sapphire), $CaTiO_3$, $BaTiO_3$, usually utilized in the manufacture of recording and/or reading heads on magnetic means or as supports of pins for horology or precision mechanics.

Examples of surfaces of the chemical individuals listed under (d) are the synthetic polymers, also of the elastomeric type, such as polyamides, polyimides, polyetherketones, aromatic polyethersulphones, polysulphones, polycarbonates, polyacetals, and in general the technopolymers utilized for the manufacture of motion members in the mechanical, aeronautical, horology fields, and furthermore the fluorinated, silicone, acrylic, nitrilic rubbers. In their utilization as lubricants for such polymers, the products of the present invention can be admixed to the polymers in amounts of from 0.5 to 5% by weight, prior to calendering, banburizing or extrusion operations, or they can be applied onto the surface of the polymeric articles ready for use.

The compounds of formula (I) or (II) protect the surfaces coated by them from the wear, when such surfaces are subjected to sliding, rolling, tangential or normal stresses, or to any movement susceptible of repeating continuous or discontinuous contact by other surfaces, which may consist of the same materials listed under (a), (b), (c). The lubricating action of compounds (I) and (II) is exerted when they are deposited onto the abovesaid materials in continuous layers having thicknesses ranging from a few tens to a few thousands of Å. Such lubricating action is exerted also on surfaces of synthetic polymers, such as the ones listed under (d).

In particular the compounds according to the present invention, when deposited onto the surface of the chemical individuals listed under (a), have the capability of protecting such surfaces from the action of atmospheric agents even in the presence of high humidity.

The products of the invention may be used also to promote the residence, on the surfaces of the materials listed under (a), (b), (c), (d), of layers of neutral perfluoropolyethers provided with a structure of type ($C_1$), ($C_2$), ($C_3$), as specified hereinbelow, which are well known as lubricants endowed with a considerable thermal and chemical stability.

($C_1$): $R_f-O(C_3F_6O)_m(CF_2O)_nR'_f$ wherein:
$R_f = CF_3, C_2F_5, C_3F_7$,
$R'_f$ = an organic radical like or different from $R_f$; m is an integer from 8 to 100, extremes included; n may be equal to or different from zero, wherefore, if n=zero, $R_f$ is preferably $=C_3F_7$, while $R'_f=C_2F_5$ or $C_3F_7$; while if n is different from zero, the m/n ratio ranges from 5 to 20, extremes included, while the sum m+n ranges from 10 to 100, extremes included;

($C_2$): $R''_f-O-(C_2F_4O)_p(CF_2O)_qR'''_f$ wherein:
$R''_f$ and $R'''_f$, like or unlike each other, may be $-CF_3$ or $-C_2F_5$, the p/q ratio ranges from 0.5 to 5 and the sum p+q ranges from 20 to 200, extremes included.

($C_3$): $R''_f-O-(C_2F_4O)_r(CF_2O)_s(C_3F_6O)_vR'''_f$ wherein:
$R''_f$ and $R'''_f$, like or unlike each other, are the same as in the preceding structure, the r/s ratio varies from 0.5 to 5, the v/r+s ratio varies from 0.01 to 0.4 and the sum v+r+s varies from 10 to 300, extremes included.

The mixtures of the products of formula (I) and/or (II) with the neutral oils of types ($C_1$), ($C_2$), ($C_3$) described hereinabove may include from 1% to 50% by weight, but preferably from 1% to 10% by weight of products (I) and/or (II).

In such mixtures, the lubricating action is improved even for thin thicknesses of the layer which are ranging from 5–10 Å to a few thousands of Å, and in sliding or rolling conditions between two surfaces even in a very rapid reciprocating motion, up to 5–10 km/minute.

The capability of the abovesaid mixtures of forming thin layers permanently adsorbed on surfaces of type (a), (b) and (c) is determined by vertical spreading measurements performed by immersing a minor side of a rectangular lamina (15×100×1 mm) made of a material of type (a), (b) or (c) into pans containing lubricants and by measuring the thickness of the lubricating film which forms in the course of time at different distances from the free surface of the lubricating liquid in the pan. Such thickness can be determined by ESCA analysis, or by FT-IR spectrophotometry by reflection on the examined surface.

The mechanical resistance of the films consisting of the compounds according to the present invention was checked by interposing dosed amounts of the compounds between two laminas of the metals listed under (a) and connected with an electric circuit in order to measure the resistance opposed by the film to the passage of the electric current: one of the two laminas was subjected to a known load (0.5 kg) and to a reciprocating motion with a stroke of 0.5 mm at a known frequency (2–50 Hz). One may notice that the electric resistance, which initially was infinite, remained high after tens of hours of reciprocating motion when between the metal laminas there are interposed compounds (I), (II) or the mixture thereof at 1–50% with the oils listed under (C1), (C2), (C3). The lubrication of parts in continuous or reciprocating motion, carried out by the compounds of type (I) and (II), according to the invention, or by mixtures thereof with the perfluoropolyethers of aforesaid type C, permits to avoid wearing phenomena of the sliding, rolling, vibrating parts, or on contacts subjected to repeating opening-closing cycles, thus allowing uniform performances.

Among the sectors particularly interested in the utilization as lubricants of compounds (I) and (II) there may be listed the ones of the magnetic means, of the electric ocntactors of the ball or roller bearings and of the bushes made from metals or sintered alloys, and in such case also the protective action of the compounds of formula (I) and (II) against the atmospheric agents is very effective.

In particular in the range of the magnetic means, the surface to be protected from the wear caused by the contact with the reading head consists of a magnetic pigment film, dispersed in a polymeric matrix, as is described under point (b).

The lubricating film based on compounds (I), (II) according to the present invention, or on mixtures thereof with the perfluoropolyethereal oils of type (C) is applicable by immersion, spreading or spraying of products as such or of dilute solutions thereof, for example at 0.5–5% of the lubricating compounds or mixtures, in 1,1,2-trichlorotrifluoroethane, and by subsequent evaporation of the solvent.

The same lubricant application technique is adopted when the magnetic material is of the metallic type, i.e. it consists of thin layers of metals such as Co—Ci, Co—Ni, Co—Ni—P deposited, as is described under point (a), onto rigid or flexible carriers, by under-vacuum evaporation, sputtering or electrodeposition techniques.

The lubrication of the magnetic means by the compounds of type (I), (II) or by mixtures thereof with the perfluorinated oils of type (C) permits to overcome, in the case of metal flexible discs, endurance tests of the order of 3–10 millions of passages on the same path by the reading head which is usually based on synthetic $Al_2O_3$, on $BaTiO_3$ or $CaTiO_3$.

The wearing resistance of the magnetic tapes was measured by subjecting the tape, either or not lubricated with the compounds of the present invention, maintained in reciprocating motion with a stroke of 6.78 cm under the tension of a force of 226.8 g applied for a tape width of 1.27 cm, to the action of a steel ball having a 8 mm diameter and loaded by a 78 g load until passage of light through the carrier surface is observed, after the magnetic layer had been removed by wear.

The compounds of structure (I) and (II) and the mixtures thereof with the perfluorinated oils of type (C) are useful to form thin protective layers against the wear due to sliding or to contact, on electric contactors where the parts intended for the contact for the electric current passage are composed of noble metals such as Au, Ag, Pt or of alloys containing Au and Ag.

In this case too, the lubricating film is deposited by immersion or spraying with a solution of the lubricant in 1,2,3-trichlorotrifluoroethane.

In the case of the electromagnetic contactors with lamellar-type nuclei, the compounds of structure (I), (II) and the mixtures thereof with compounds (C) efficaciously damp the vibrations of the contactor.

The compounds of the present invention are useful as lubricants of manufactured articles based on technopolymers subjected to movement and to contact with other surfaces.

Examples of such manufactured articles are gears, porous bushes, sliders, contacts, components of ball or roller bearings.

The compounds of the present invention are also usefully included in the formulation of greases consisting of suspending liquids of apolar nature, and of thickners consisting of organic polymeric materials or of inorganic materials.

The effect of the compounds of structure (I) and (II) is that of enhancing the mechanical stability of the greases, of reducing the oil leak during work, of increasing the anti-wear effect. Examples of the greases which are susceptible of being improved by the compounds forming the object of the present invention, used in percentages of from 0.1 to 2%, are the greases formulated with mineral, silicone or perfluoropolyethereal oils and thickened with PTFE, TFE-EFP copolymers (FEP), silica, graphite, $MoS_2$, bentonites.

The compounds of formula (I) and (II), which are the object of this invention, can be prepared starting from known compounds having respectively the following structures:

($D_1$): $RO(C_3F_6O)_m(CFXO)_nCFX$—K ($D_2$): $R''CFXO(C_3F_6O)_x(CFXO)_y(C_2F_4O)_zCFX$—K wherein: m, n, R, R'', X, x, y, z are the same as defined hereinbefore, and R'' may be also equal to K, and wherein K is a functional group of the type

—COOM (M=H, $CH_3$),

—CHO,

—$CH_2OH$,

—COCl,

—COF, by reaction with compounds of formula D—Y, where Y has the meaning previously specified and D is a functional group capable of reacting with group K to yield A. The compounds in which A=—$CH_2O$— are obtained from the precursors of formula $D_1$ or $D_2$ in which K=—$CH_2OH$, by condensation in an alkaline medium with products containing group YCl with movable halogen.

The compounds in which A=—$CH_2OCH_2$— are usually obtained still from hydroxymethyl precursors of formula $D_1$ or $D_2$ by alkaline condensation with compounds containing a chloro- or bromomethylated aromatic ring in group Y.

The compounds in which A=$CF_2O$— are obtained from precursors $D_1$ or $D_2$ in which K=ester group (obtained from compounds $D_1$ or $D_2$ where K=—COOH, or —COO—alkyl, or also —COCl, by reaction with compounds of formula Y—OH) by fluorination of group =C=O to —$CF_2$— with HF/$SF_4$— mixtures, at temperatures from 120° to 180° C. and at pressures from 20 to 60 atm., with reaction times of 20-25 hours, following under I.R. the disappearance of the absorption due to group CO.

The compounds where A=—$CF_2$— are obtained by reaction of precursors $D_1$ or $D_2$, in which K=—COCl or —COF, with products of formula DY, wherein D is a metal of the type Li, Mg, Cu, under known conditions for obtaining ketone compounds of formula $D_1$—CO—Y or $D_2$—CO—Y, carrying then out the conversion of group =C=O to —$CF_2$ with HF/$SF_4$- mixtures, at temperatures from 120° to 180° C. and at pressures from 20 to 60 atm., with reaction times of 20-25 hours following under I.R. the disappearance of the absorption due to group =CO.

The following examples are given to illustrate the present invention, without being however a limitation thereof.

EXAMPLE 1

75 g of a diol of formula

HOCH$_2$—CF$_2$O—(C$_2$F$_4$O)$_m$—(CF$_2$O)$_p$—CF$_2$—CH$_2$—OH (where m+p=25, m/p=0.6) having a M.W.=2300, were added to a solution of 8 g of potassium terbutylate in 150 cc of ter. butyl alcohol maintained at 30° C.

Stirring was carried on for 2 hours. Successively, 13 g of 4-chloromethyl-1,2-methylenedioxybenzene were added. Precipitation of potassium chloride was immediately observed. Reaction was continued during 3 hours, always at 30° C., then the reaction mixture was poured into water containing 0.4% of hydrochloric acid.

The layers then separated; the heaviest one, after drying under the vacuum created by a mechanical pump at 100° C., was filtered on a membrane. Thus, there were obtained 76 g of a limpid liquid which, on I.R. and N.M.R. analyses, proved to consist of a compound having the following structure:

$$\underset{O}{\overset{O}{CH_2}}\!\!\!\diagup\!\!\!\diagdown\text{—CH}_2\text{OCH}_2\text{CF}_2(\text{C}_2\text{F}_4\text{O})_m(\text{CF}_2\text{O})_p\text{CF}_2\text{CH}_2\text{OCH}_2\text{—}\!\!\!\diagup\!\!\!\diagdown\underset{O}{\overset{O}{CH_2}}$$

A magnetic tape with CrO$_2$ pigment was spread on a reverse roll coater with a 1% solution of such compound in 1,1,2-trichlorotrifluoroethane. A specimen of a tape so treated was subjected to the abrasion action of a steel ball having a 0.32 mm diameter, loaded with a 28 g load. The ball was subjected to a reciprocating motion along a 6.78 cm run. The tape was under a tension caused by a force equal to 226.8 g applied onto a tape width equal to 1.27 cm.

After a time corresponding to 8000 passages no signs of abrasion were noticed, while after 350 passages the non-lubricated tape exhibited signs of abrasion revealed by the passage of light.

The derivatives of this example was also utilized in the lubrication of metallised floppy disks prepared by sputtering of two layers (lower layer made of permalloy and upper layer made of Co—Cr).

The coating with lubricant was carried out by dip coating in a 1% solution of the compound in 1,1,2-trichlorotrifluoroethane. At an extraction speed of 5 mm/sec. the resulting thickness was of about 500 Å. After rotation in a liner, the actual thicknesses were of about 200 Å. The discs so lubricated were subjected to wearing tests according to standard ANSI through rotation on the same path until the limit of 3 millions of revolutions.

Under a 15 g load of the head, the disc resisted during 4.2 millions of revolutions before showing signs of wear detectable by optical microscopy. A subsequent examination with an E.D.S. microfeeler proved that the wear was only superficial and had not affected the Co—Cr layer until bringing to surface the permalloy the underlayer.

A 2% solution of compound (b) in 1,2-trichlorotrifluoroethane was utilized to lubricate the surface of a video tape prepared by depositing (by means of the high incidence deposition technique) a layer of Co—Ni alloy having a thickness of 0.2μ onto a polyester resin film having a thickness of 12μ.

Two tape samples, one of which was lubricated and the other not lubricated, were subjected to comparative friction coefficient and still frame life tests.

The (dynamic) friction coefficient measured between non-lubricated tape and a ceramic slider resulted to be equal to 0.55. The same determination on the tape lubricated by the derivative in question led to a friction coefficient of 0.2.

The still frame tests showed that the non-lubricated tape was not capable of withstanding the still frame run for more than 10 seconds, while the lubricated tape was able to run during 5 minutes under the same conditions without serious damages and with an absolutely acceptable drop-out rate.

EXAMPLE 2

45 g of a compound of formula $$C_3F_7O(\underset{\underset{CF_3}{|}}{CF}\text{—}CF_2O)_4\underset{\underset{CF_3}{|}}{CF}\text{—}CH_2OH$$

having a M.W.=980 were added to a solution of 5.5 g of potassium ter. butylate in 100 cc of ter.butyl alcohol, maintained at 30° C. After a 2-hour reaction, 5.5 g of 4-chloromethyl-1,2-methylenedioxybenzene were added, the whole was stirred during 3 hours at 30° C., whereafter the mixture was poured into 200 cc of an aqueous solution at 0.4% of hydrochloric acid. The heaviest layer formed was then separated, which, after concentration by evaporation at 100° C. under vacuum, was filtered on a membrane. 43 g of a limpid liquid were thus obtained which, on I.R. and N.M.R. analyses, revealed to consist of the compound of formula:

$$C_3F_7O\text{—}(\underset{\underset{CF_3}{|}}{CF}CF_2O)_4\underset{\underset{CF_3}{|}}{CF}\text{—}CH_2OCH_2\text{—}\!\!\!\diagup\!\!\!\diagdown\underset{O}{\overset{O}{CH_2}}$$

A 1% solution of such compound in 1,1,2-trichlorotrifluoroethane was used to coat floppy disks of the same type as described in example 1. The disks, treated in like manner as described in said example and subjected to wearing tests according to ANSI standards, revealed wear signs under the optical microscope after 3.5 million rotations on the same path.

A mild steel lamina measuring 3×50×100 mm, polished and cleaned from oily residues, if any, was immersed into the product obtained as described hereinbefore and was extracted at a speed of 10 mm/sec. It was allowed to stand for 12 hours, whereafter it was kept during 28 hours in a non-saline mist chamber at 50° C. and at 100% of relative humidity.

At the end of the test, the lamina did not exhibit rust traces.

For comparison purposes, a lamina treated in the same manner in a fluoroethereal oil, "Fomblin" type, having a viscosity of 250 Cst. at 20° C., exhibited evident rust signs at the end of the test.

We claim:

1. Magnetic recording media provided with a coating on the whole surface thereof having a thickness of from a few tens to a few thousands of Angstrom units, and comprising at least one compound selected from the class of compounds having the formula:

$$RO(C_3F_6)_m-(CFXO)_n-CFX-L, \quad (I)$$

and $$R''CFXO-(C_3F_6O)_x-(CFXO)_y-(C_2F_4O)_z-CFX-L, \quad (II)$$

where
- $R = -CF_3, -C_2F_5, -C_3F_7$,
- $X = F, -CF_3$,
- $R'' = F, -CF_3, -C_2F_5$,
- m = an integer from 3 to 100,
- n = an integer, either finite or equal to zero, where m+n ranges from 3 to 100, provided that, if n is finite, then m/n ranges from 5 to 20 and R is preferably $-CF_3$, while if n = zero, R is preferably $-C_2F_5$ or $-C_3F_7$,
- x = an integer, either finite or equal to zero,
- y,z = finite integers, such that x+y+z ranges from 5 to 200, while x+z ranges from 5 to 0.5, provided that when x = zero, z/y ranges from 1 to 0.5 and y+z ranges from 5 to 200, while x is preferably F, and R'' = L,
- L = a group of A—Y, where
  - A = $-CH_2O-$, $-CH_2-O-CH_2$, $-CF_2$, $-CF_2O-$,
  - Y = an organic radical having one of the following formulas:

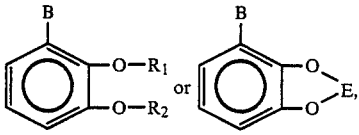

where
- $R^1, R_2 = C_1-C_3$ alkyl,
- E = $-CHR_3-$ or $-CH_2-CHR_3-$,
- $R_3$ = H or an alkyl $C_1-C_3$, and
- B = H or a radical $-OR_3$.

2. A mixture including at least one of the compounds according to claim 1 and at least one neutral perfluoropolyether having perfluoroalkyl end groups, said perfluoropolyether being present in the mixture in an amount of from about 50% to about 99% by weight.

* * * * *